(12) United States Patent
Kent et al.

(10) Patent No.: US 9,981,131 B2
(45) Date of Patent: May 29, 2018

(54) SYSTEMS AND METHODS FOR DETERMINING SPINAL CORD STIMULATION PARAMETERS BASED ON PATIENT FEEDBACK

(71) Applicant: Pacesetter, Inc., Sunnyvale, CA (US)

(72) Inventors: Alexander Kent, Mountain View, CA (US); Edward Karst, Los Angeles, CA (US); Gene A. Bornzin, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 110 days.

(21) Appl. No.: 14/946,538

(22) Filed: Nov. 19, 2015

(65) Prior Publication Data

US 2017/0143971 A1 May 25, 2017

(51) Int. Cl.
| | | |
|---|---|---|
| *A61B 5/103* | (2006.01) | |
| *A61B 5/117* | (2016.01) | |
| *A61N 1/36* | (2006.01) | |
| *A61B 5/00* | (2006.01) | |
| *A61B 5/053* | (2006.01) | |

(Continued)

(52) U.S. Cl.
CPC ........ *A61N 1/36132* (2013.01); *A61B 5/0533* (2013.01); *A61B 5/225* (2013.01); *A61B 5/4824* (2013.01); *A61N 1/36062* (2017.08); *A61B 5/4836* (2013.01); *A61B 2562/046* (2013.01); *A61N 1/0551* (2013.01); *A61N 1/36021* (2013.01); *A61N 1/36071* (2013.01);
(Continued)

(58) Field of Classification Search
CPC ............ A61N 1/36071; A61N 1/36132; A61N 1/36135; A61N 1/37247; A61N 1/36021; A61B 5/0533; A61B 5/225; A61B 5/4824; A61B 5/4836; G06F 3/015; A63B 21/4035
See application file for complete search history.

(56) References Cited

U.S. PATENT DOCUMENTS

| | | |
|---|---|---|
| 7,212,110 B1 | 5/2007 | Martin et al. |
| 7,228,179 B2 | 6/2007 | Campen et al. |

(Continued)

FOREIGN PATENT DOCUMENTS

| | | |
|---|---|---|
| WO | 2001/093953 | 12/2001 |

OTHER PUBLICATIONS

Al-Kaisy A, Palmisani S, Smith T, Harris S, Pang D, "The use of 10-kilohertz spinal cord stimulation in a cohort of patients with chronic neuropathic limb pain refractory to medical management," Neuromodulation, 18: 18-23, 2015.
de Vos CC, Bom MJ, Vanneste S, Lenders MW, de Ridder D, "Burst spinal cord stimulation evaluated in patients with failed back surgery syndrome and painful diabetic neuropathy," Neuromodulation, 17(2): 152-9, 2014.
Kumar K, Caraway DL, Rizvi S, Bishop S, "Current challenges in spinal cord stimulation," Neuromodulation, 17: 22-35, 2014.

(Continued)

*Primary Examiner* — Devin Henson
(74) *Attorney, Agent, or Firm* — Theresa A. Raymer

(57) ABSTRACT

The present disclosure provides a grip sensor for quantifying pain experienced by a patient during spinal cord stimulation (SCS). The grip sensor includes an electronics enclosure, an annular outer shell substantially surrounding the electronics enclosure and sized to be held by the patient, a pressure sensor embedded in the outer shell and communicatively coupled to the electronics enclosure, the pressure sensor configured to measure a grip strength of the patient as SCS is applied to the patient, and a plurality of galvanic skin response sensors communicatively coupled to the electronics enclosure and configured to measure an electrical impedance of the skin of the patient as SCS is applied to the patient.

11 Claims, 11 Drawing Sheets

(51) Int. Cl.
  *A61B 5/22* (2006.01)
  *A61N 1/05* (2006.01)
  *G06F 3/01* (2006.01)
  *A61N 1/372* (2006.01)
  *A63B 21/00* (2006.01)

(52) U.S. Cl.
  CPC ...... *A61N 1/36135* (2013.01); *A61N 1/37247* (2013.01); *A63B 21/4035* (2015.10); *G06F 3/015* (2013.01)

(56) References Cited

U.S. PATENT DOCUMENTS

| | | | |
|---|---|---|---|
| 7,571,007 | B2 | 8/2009 | Erickson et al. |
| 9,357,949 | B2* | 6/2016 | Drew .................. A61B 5/061 |
| 2006/0170486 | A1 | 8/2006 | Tranchina et al. |
| 2011/0072657 | A1 | 3/2011 | Swanson et al. |
| 2012/0310305 | A1* | 12/2012 | Kaula .............. A61N 1/36071 607/60 |
| 2013/0046205 | A1* | 2/2013 | Schaffner ............ A61B 5/4824 600/587 |
| 2016/0213314 | A1* | 7/2016 | Zuckerman-Stark A61B 5/7264 |

OTHER PUBLICATIONS

Molnar G and Giancarlo B, "Principles of cord activation during spinal cord stimulation," Neuromodulation, 17: 12-21, 2014.

Schu S, Slotty PJ, Bara G, von Knop M, Edgar D, Vesper J, "A prospective, randomized, double-blind, placebo-controlled study to examine the effectiveness of burst spinal cord stimulation patterns for the treatment of failed back surgery syndrome," Neuromodulation, 17: 443-50, 2014.

Sharan A, Cameron T, Barolat G, "Evolving patterns of spinal cord stimulation in patients implanted for intractable low back and leg pain," Neuromodulation, 5(3): 167-79, 2002.

Tiede J, Brown L, Gekht G, Vallejo R, Yearwood T, Morgan D, "Novel spinal cord stimulation parameters in patients with predominant back pain," Neuromodulation, 16: 370-5, 2013.

Van Havenbergh T, Vancamp T, Van Looy P, Vanneste S, de Ridder D, "Spinal cord stimulation for the treatment of chronic back pain patients: 500-Hz vs. 1000-Hz burst stimulation," Neuromodulation, 18: 9-12, 2015.

* cited by examiner

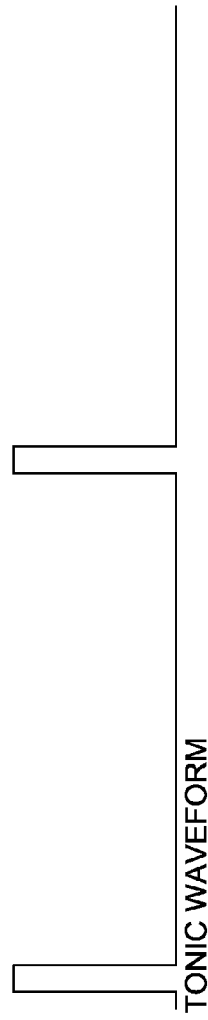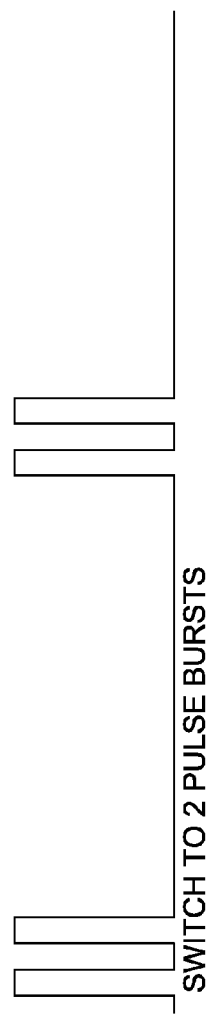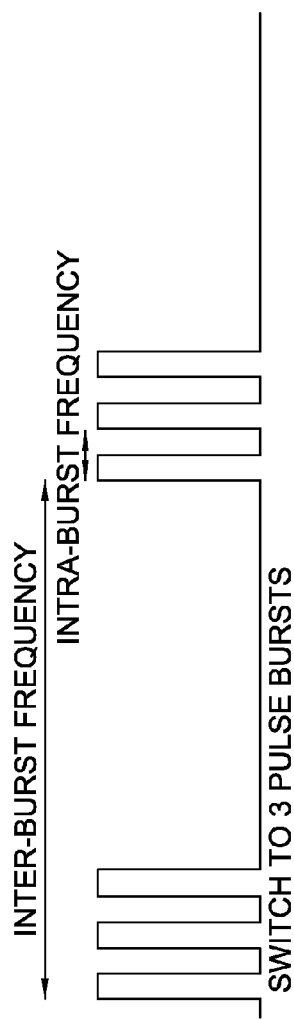

SYSTEMS AND METHODS FOR DETERMINING SPINAL CORD STIMULATION PARAMETERS BASED ON PATIENT FEEDBACK

A. FIELD OF THE DISCLOSURE

The present disclosure relates generally to neurostimulation systems, and more particularly to determining stimulation parameters and quantifying patient pain for spinal cord stimulation.

B. BACKGROUND ART

Neurostimulation is a treatment method utilized for managing the disabilities associated with pain, movement disorders such as Parkinson's Disease (PD), dystonia, and essential tremor, and also a number of psychological disorders such as depression, mood, anxiety, addiction, and obsessive compulsive disorders.

At least some known neurostimulation systems are closed-loop spinal cord stimulation (SCS) systems based on neurological sensing systems. In at least some known systems, selecting parameters for SCS relies on a "guess-and-check" approach to find therapeutically effective parameter sets for chronic pain. For example, for traditional tonic (i.e., single pulse) stimulation waveforms, there are several parameters that can be independently tuned, including stimulation amplitude, pulse width, frequency, and contact configuration (e.g., the location of cathodes and anodes). Moreover, with the introduction of other stimulation waveforms, such as burst stimulation, there are even more parameters to tune, including inter-burst and intra-burst frequency. Finally, it is also desirable to determine which stimulation waveform (tonic, burst, etc.) generates the best response in each individual patient. In at least some known systems, however, the process for selecting stimulation parameters may not be well-defined for efficiently and rationally identifying parameters that facilitate generating optimal therapy.

In tonic SCS, stimulation parameters may be adjusted until there is paresthesia coverage of painful regions of the patient's body. The stimulation amplitude generally determines the extent of neuronal activation. Accordingly, in at least some known systems, amplitude is titrated between a perception threshold (i.e., a level at which the patient senses paresthesia) and a discomfort threshold (i.e., a level at which the patient experiences discomfort). The discomfort threshold may be, for example, 1.4 to 1.7 times the perception threshold. In addition, pulse width may be adjusted. Increasing pulse width generally leads to smaller differences in stimulation thresholds between large and small diameter fibers.

In high-frequency SCS, a tonic waveform may be applied at frequencies in the 2 to 10 kilohertz (kHz) range to generate pain relief with reduced paresthesia. For example, for 10 kHz stimulation, amplitude may be 0.5 to 5 milliamps (mA) and pulse width may be 30 microseconds (μs). Paresthesia mapping is not generally used for high-frequency SCS, and instead, a stimulation site is more consistent, with stimulation typically applied at C4-C5 for chronic pain of the upper limbs/hands, and at T8-T12 for the back and lower limbs.

For burst SCS, a waveform including packets of high-frequency pulses that are separated by a quiescent period is used. Burst SCS often results in paresthesia-free stimulation. Typical waveform parameters may be, for example, a 500-1000 hertz (Hz) intra-burst frequency, a 40 Hz intra-burst frequency, five pulses per burst, and 0.5-1 millisecond (ms) pulse width. The amplitude is typically subsensory (e.g., 90% of the paresthesia threshold), and may average around 3.4 mA.

In addition to selecting parameters, another difficulty in SCS programming arises when attempting to quantify patient pain. For example, patients may be asked to quantify their pain on a scale of 1 to 10, state their percentage pain relief compared to baseline, and/or identify body locations where pain relief and paresthesia are felt. The patient must continuously provide these subjective measures with each parameter adjustment, which can be time-consuming for both the patient and the programmer. Moreover, the reliability of these subjective pain measures is questionable.

Further, when delivering SCS stimulation, it may be desirable to extend the battery life of one or more components of an SCS system. As such, there is a need to identify SCS waveforms that provide substantially paresthesia-free stimulation while minimizing the amount of energy delivered.

BRIEF SUMMARY OF THE DISCLOSURE

In one embodiment, the present disclosure is directed to a grip sensor for quantifying pain experienced by a patient during spinal cord stimulation (SCS). The grip sensor includes an electronics enclosure, an annular outer shell substantially surrounding the electronics enclosure and sized to be held by the patient, a pressure sensor embedded in the outer shell and communicatively coupled to the electronics enclosure, the pressure sensor configured to measure a grip strength of the patient as SCS is applied to the patient, and a plurality of galvanic skin response sensors communicatively coupled to the electronics enclosure and configured to measure an electrical impedance of the skin of the patient as SCS is applied to the patient.

In another embodiment, the present disclosure is directed to a system for quantifying pain experienced by a patient during spinal cord stimulation (SCS). The system includes a grip sensor sized to be gripped by the patient and comprising at least one sensor configured to measure at least one value as different SCS configurations are applied to the patient, a computing device communicatively coupled to the grip sensor and configured to calculate a pain level for each SCS configuration based on the at least one value measured by the at least one sensor, and a display device communicatively coupled to the grip sensor and configured to display a plot including the calculated pain level for each SCS configuration.

In another embodiment, the present disclosure is directed to a method for determining SCS therapy parameters for a patient. The method includes applying tonic stimulation at a fixed frequency, varying at least one parameter of the applied tonic stimulation until paresthesia coverage of a target area of the patient is achieved, and further manipulating the applied tonic stimulation to achieve one of burst stimulation and high-frequency stimulation that provides pain relief with reduced paresthesia.

The foregoing and other aspects, features, details, utilities and advantages of the present disclosure will be apparent from reading the following description and claims, and from reviewing the accompanying drawings.

BRIEF DESCRIPTION OF THE DRAWINGS

FIGS. 6A-6C are diagrams illustrating operation of one embodiment of a burst stimulation algorithm.

Corresponding reference characters indicate corresponding parts throughout the several views of the drawings.

DETAILED DESCRIPTION OF THE DISCLOSURE

The present disclosure provides programming algorithms for semi-autonomous and rapid determination of therapeutically effective stimulation parameters. These algorithms rely on signals obtained from a hand-held grip sensor. This allows patients to provide real-time, quantitative feedback on pain level as parameters are adjusted, as described herein.

Neurostimulation systems are devices that generate electrical pulses and deliver the pulses to nerve tissue of a patient to treat a variety of disorders. Spinal cord stimulation (SCS) is the most common type of neurostimulation within the broader field of neuromodulation. In SCS, electrical pulses are delivered to nerve tissue of the spinal cord for the purpose of chronic pain control. While a precise understanding of the interaction between the applied electrical energy and the nervous tissue is not fully appreciated, it is known that application of an electrical field to spinal nervous tissue can effectively inhibit certain types of pain transmitted from regions of the body associated with the stimulated nerve tissue to the brain. Specifically, applying electrical energy to the spinal cord associated with regions of the body afflicted with chronic pain can induce "paresthesia" (a subjective sensation of numbness or tingling) in the afflicted bodily regions.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals (also electrically coupled to the wire conductors) that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

Figure 1:
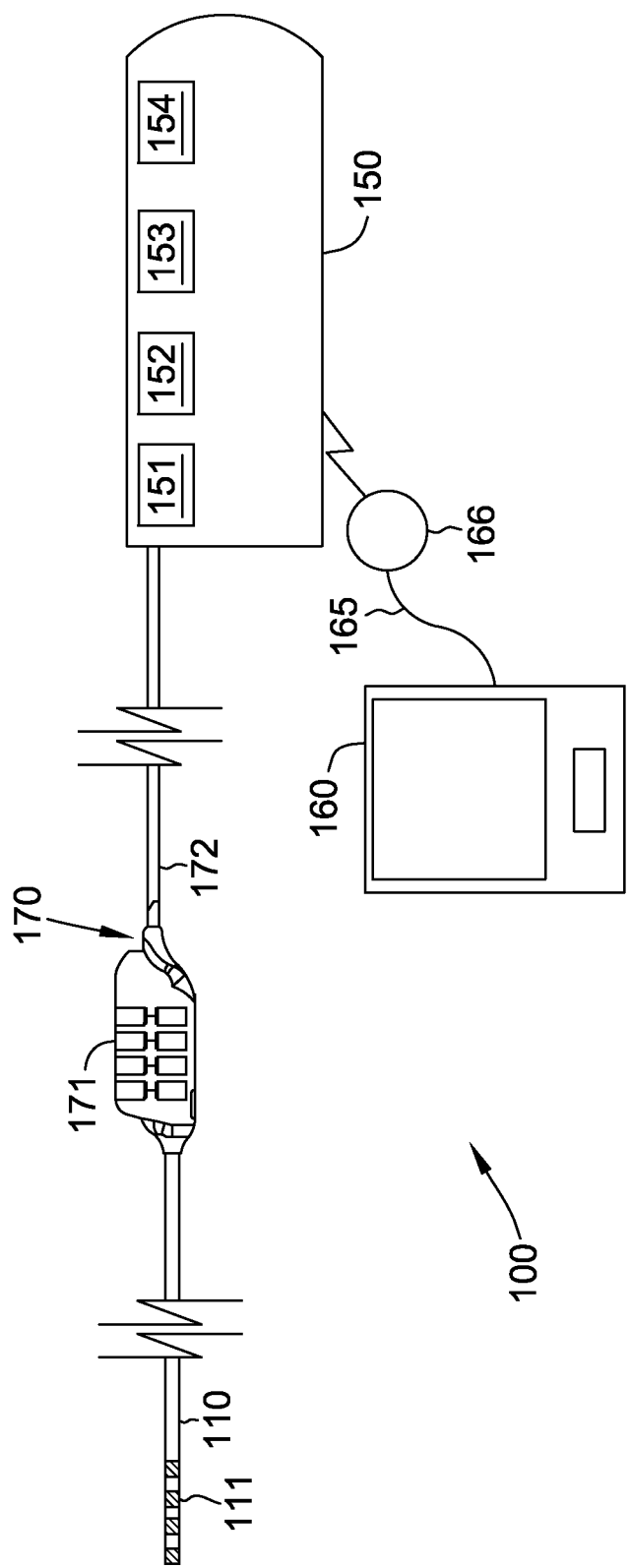
FIG. 1 is a schematic view of one embodiment of a stimulation system.

Referring now to the drawings, and in particular to FIG. 1, a stimulation system is indicated generally at 100. Stimulation system 100 generates electrical pulses for application to tissue of a patient, or subject, according to one embodiment. Stimulation system 100 includes an implantable pulse generator (IPG) 150 that is adapted to generate electrical pulses for application to tissue of a patient. Implantable pulse generator 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of implantable pulse generator 150 for execution by the microcontroller or processor to control the various components of the device.

Implantable pulse generator 150 may comprise one or more attached extension components 170 or be connected to one or more separate extension components 170. Alternatively, one or more stimulation leads 110 may be connected directly to implantable pulse generator 150. Within implantable pulse generator 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from implantable pulse generator 150 and conducted through the conductors of lead body 172 are provided to stimulation lead 110. The pulses are then conducted through the conductors of stimulation lead 110 and applied to tissue of a patient via electrodes 111. Any suitable known or later developed design may be employed for connector portion 171.

For implementation of the components within implantable pulse generator 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within implantable pulse generator 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of stimulation lead 110 to its distal end. The conductors electrically couple a plurality of electrodes 111 to a plurality of terminals (not shown) of stimulation lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

Figure 2A:
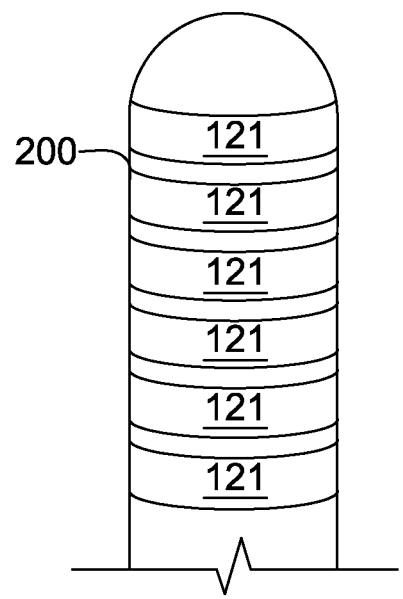
FIGS. 2A-2C are schematic views of stimulation portions that may be used with the stimulation system of FIG. 1.
Figure 2B:
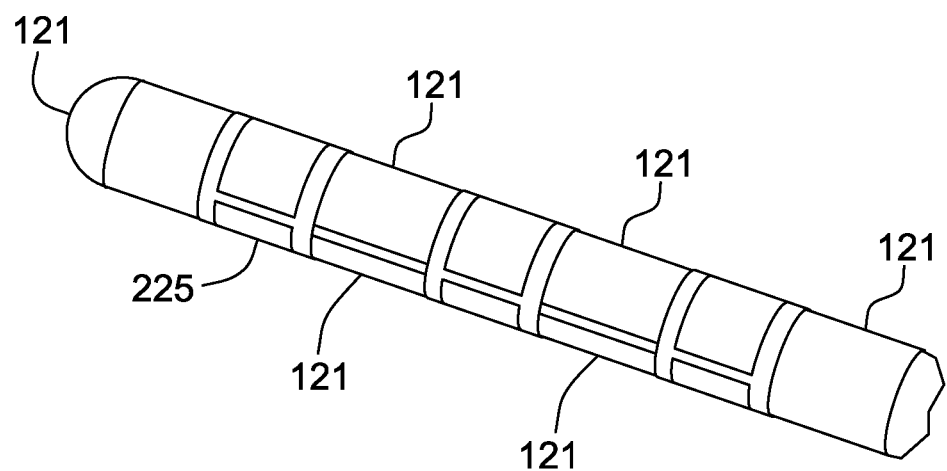
Figure 2C:
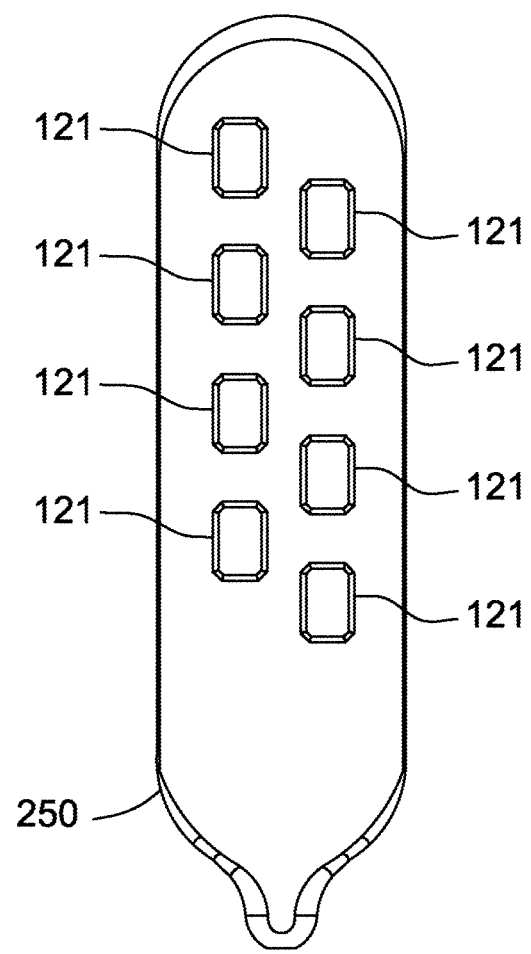

FIGS. 2A-2C respectively depict stimulation portions 200, 225, and 250 for inclusion at the distal end of stimulation lead 110. Stimulation portions 200, 225, and 250 each include one or more electrodes 121. Stimulation portion 200 depicts a conventional stimulation portion of a "percutaneous" lead with multiple ring electrodes. Stimulation portion 225 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Patent Publication No. 2011/0072657, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Controller device 160 (shown in FIG. 1) may be implemented to recharge battery 153 of implantable pulse generator 150 (although a separate recharging device could alternatively be employed). A "wand" 165 may be electrically connected to controller device 160 through suitable electrical connectors (not shown). The electrical connectors are electrically connected to a "primary" coil 166 at the distal end of wand 165 through respective wires (not shown). Typically, primary coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through primary coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery of implantable pulse generator 150. The charging circuitry may also communicate status messages to controller device 160 during charging operations using pulse-loading or any other suitable technique. For example, controller device 160 may communicate the coupling status, charging status, charge completion status, etc.

External controller device 160 is also a device that permits the operations of implantable pulse generator 150 to be controlled by user after implantable pulse generator 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with implantable pulse generator 150.

Controller device 160 preferably provides one or more user interfaces to allow the user to operate implantable pulse generator 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. Implantable pulse generator 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Example commercially available neurostimulation systems include the EON MINI™ pulse generator and RAPID PROGRAMMER™ device from St. Jude Medical, Inc. (Plano, Tex.). Example commercially available stimulation leads include the QUATTRODE™, OCTRODE™, AXXESS™, LAMITRODE™, TRIPOLE™, EXCLAIM™, and PENTA™ stimulation leads from St. Jude Medical, Inc.

The systems and methods described herein facilitate efficient and effective SCS parameter adjustment based on patient feedback. A grip sensor allows patients to provide quantitative feedback on their pain levels during parameter adjustment between SCS configurations (e.g., varying, amplitude, pulse width, electrode contact configuration, etc.). Further, programming algorithms facilitate selecting parameters for non-tonic SCS, including burst and high-frequency stimulation waveforms.

Figure 3:
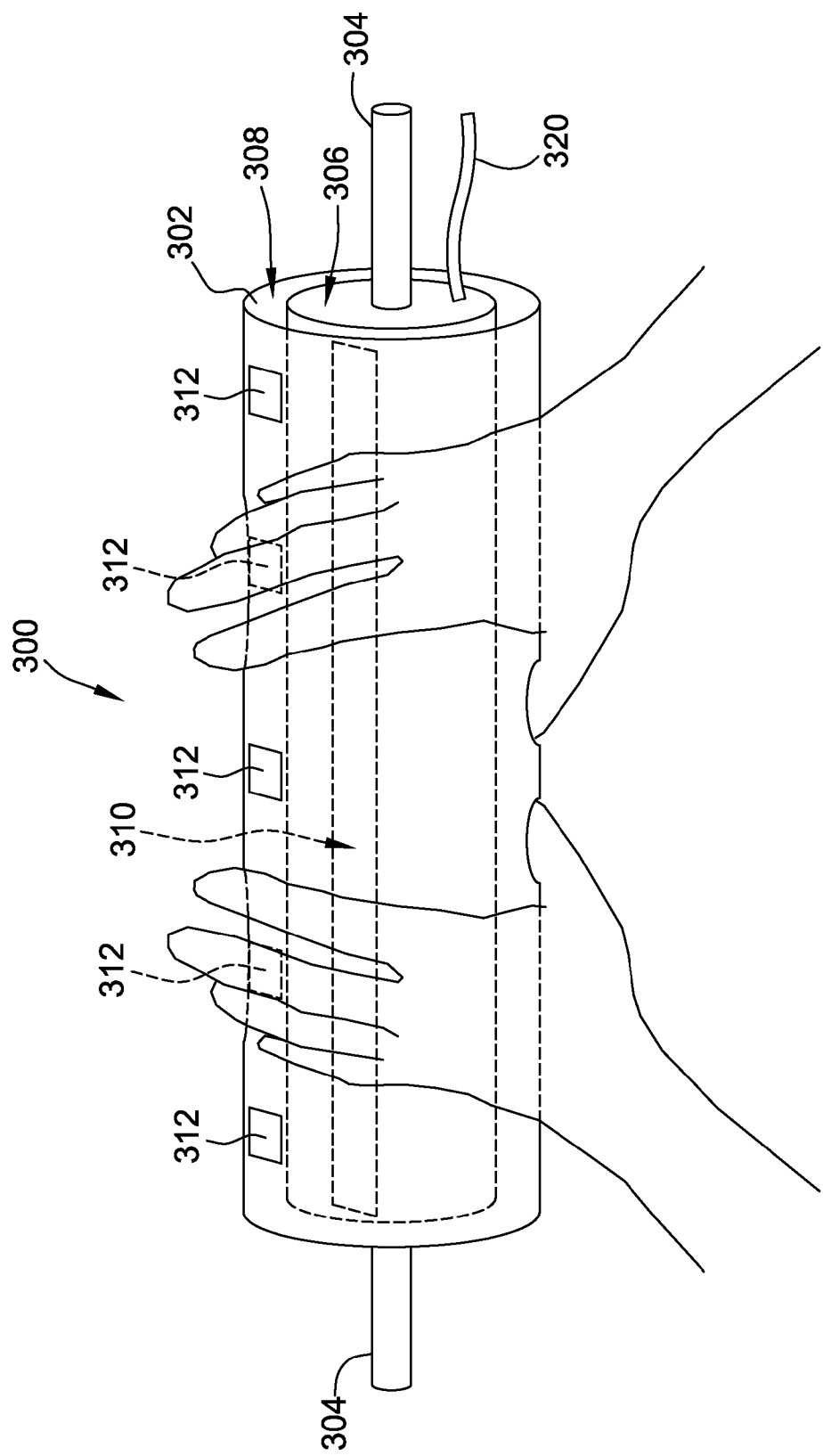
FIG. 3 is a schematic diagram of one embodiment of a grip sensor that may be used with the stimulation system of FIG. 1.

FIG. 3 is a schematic diagram of one embodiment of a grip sensor 300 that may be used to facilitate efficient and effective SCS parameter adjustment based on patient feedback. Grip sensor 300 is used during SCS programming to enable the patient to give real-time, quantitative feedback on their pain level in an office/clinical setting or remotely.

In this embodiment, grip sensor 300 includes a substantially cylindrical housing 302 and mechanical support rods 304 that extend from opposite ends of housing 302. Mechanical support rods 304 facilitate keeping grip sensor 300 elevated and in place. Housing 302 is formed by an electronics enclosure 306 and an annular outer shell 308 that substantially surrounds electronics enclosure 306. Outer shell 308, in this embodiment, is made of a deformable material (e.g., rubber, soft plastic) that has elasticity when squeezed. Grip sensor 300 is sized to be comfortably gripped by one or two hands of the patient. Alternatively, grip sensor 300 may have any suitable shape and/or configuration.

At least one pressure sensor 310 (e.g., a pressure transducer) is embedded in outer shell 308 in this embodiment. Pressure sensor 310 measures a patient's grip strength (which generally increases with pain) on grip sensor 300. Pressure sensor 310 may include a strain gauge, a variable capacitor cooperating with a diaphragm and a pressure cavity, and/or piezoelectric materials. Pressure sensor 310 is placed within or underneath outer shell 308 and extends substantially along the length of grip sensor 300 in this embodiment.

Grip sensor 300 also includes galvanic skin response (GSR) sensors 312 in this embodiment. GSR sensors 312 measure changes in an electrical impedance of the skin of the patient, which result from physiochemical responses to emotional arousal (e.g., sweating) that increase with sympathetic nervous system activity (e.g., the so-called "fight-or-flight" response). Impedance measured by GSR sensors 312 will also generally increase with a greater area of contact between GSR sensors 312 and the patient's skin. The GSR impedance will generally increase with pain. GSR sensors 312 are embedded within outer shell 308, such that surfaces of GSR sensors 312 are exposed for contact with the patient's hands. In this embodiment, a single GSR sensor or plurality of GSR sensors 312 span the length of grip sensor 300.

In some embodiments, grip sensor 300 includes other sensing devices. For example, grip sensor 300 may include a thermometer that measures a skin temperature of the patient and heat flux (i.e., the rate of heat dissipation from the patient's body) attributable to the patient. The thermometer may be a thermocouple or thermistor. The skin temperature and/or heat flux, similar to grip strength and electrical impedance, may correspond to a pain level experienced by the patient. In another embodiment, grip sensor 300 includes a heart rate sensor. The heart rate sensor may be, for example, an optical transmitter/receiver that illuminates capillaries on the hand and measures the frequency that blood pumps past the sensor. Circuitry (e.g., amplifiers, filters, analog-to-digital converters) for processing signals from the various sensors is contained within electronics enclosure 306. In this embodiment, grip sensor 300 further includes a wired connection 320 for communicatively coupling electronics enclosure 306 to a display (not shown in FIG. 3) for visualizations of measurements acquired using grip sensor 300.

Figure 4:
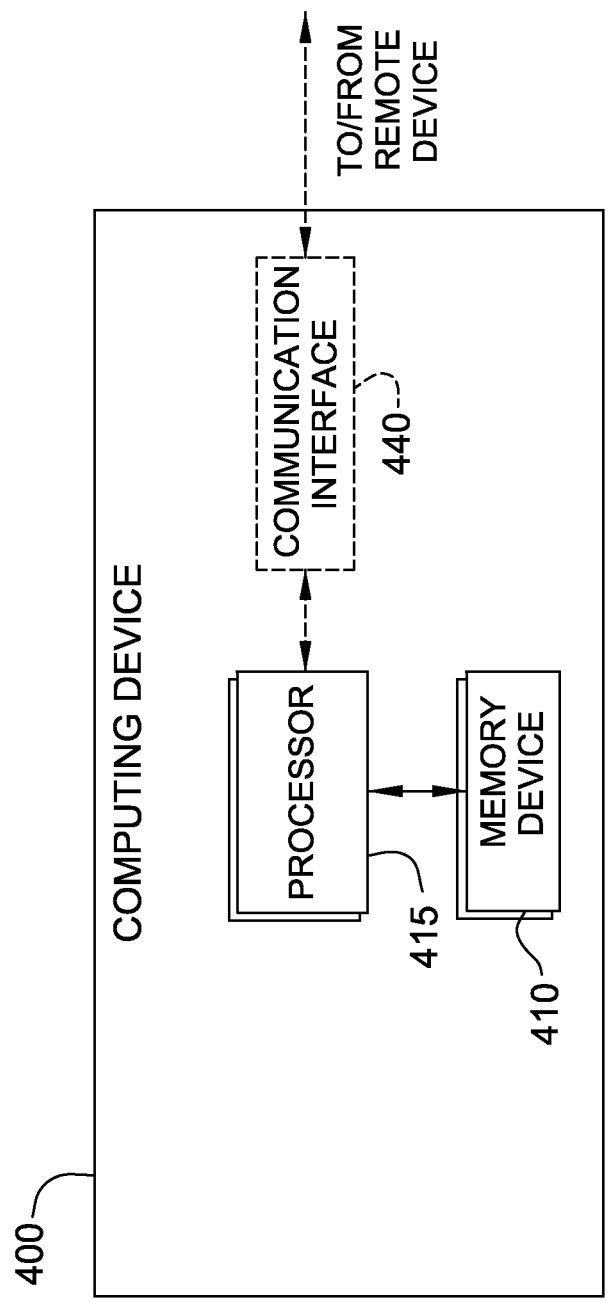
FIG. 4 is a block diagram of one embodiment of a computing device that may be used with the grip sensor shown of FIG. 3.

FIG. 4 is a block diagram of one embodiment of a computing device 400 that may be used with grip sensor 300 to facilitate processing measurements acquired using grip sensor 300. Computing device 400 may be included within grip sensor 300 (e.g., as part of electronics enclosure 306), or may be communicatively coupled (e.g., wired or wirelessly connected) to grip sensor 300.

In this embodiment, computing device 400 includes at least one memory device 410 and a processor 415 that is coupled to memory device 410 for executing instructions. In some embodiments, executable instructions are stored in memory device 410. In the illustrated embodiment, computing device 400 performs one or more operations described herein by programming processor 415. For example, processor 415 may be programmed by encoding an operation as one or more executable instructions and by providing the executable instructions in memory device 410.

Processor 415 may include one or more processing units (e.g., in a multi-core configuration). Further, processor 415 may be implemented using one or more heterogeneous processor systems in which a main processor is present with secondary processors on a single chip. In another illustrative example, processor 415 may be a symmetric multi-processor system containing multiple processors of the same type. Further, processor 415 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In the illustrated embodiment, memory device 410 is one or more devices that enable information such as executable instructions and/or other data to be stored and retrieved. Memory device 410 may include one or more computer readable media, such as, without limitation, dynamic random access memory (DRAM), read-only memory (ROM), electrically erasable programmable read-only memory (EEPROM), static random access memory (SRAM), a solid state disk, and/or a hard disk. Memory device 410 may be configured to store, without limitation, application source code, application object code, source code portions of interest, object code portions of interest, configuration data, execution events and/or any other type of data.

Computing device 400, in the illustrated embodiment, includes a communication interface 440 coupled to processor 415. Communication interface 440 communicates with one or more remote devices, such as a clinician or patient programmer. To communicate with remote devices, communication interface 440 may include, for example, a wired network adapter, a wireless network adapter, a radio-frequency (RF) adapter, and/or a mobile telecommunications adapter.

Grip sensor 300 is used in conjunction with computing device 400 for semi-autonomous and rapid determination of therapeutically effective stimulation parameters. In one example, an algorithm for rational selection of burst stimulation parameters is utilized. The burst stimulation algorithm initially identifies an optimal contact configuration, amplitude, and pulse width using tonic stimulation, and then switches each tonic pulse into multi-pulse bursts and adjusts inter-burst and intra-burst frequencies for pain relief with reduced paresthesia. In another example, an algorithm for rational selection of high-frequency stimulation parameters is utilized. The high-frequency algorithm first identifies an optimal contact configuration, amplitude, and pulse width using tonic stimulation, and then adjusts the frequency to 1 kHz and increases the frequency (or adjusts to 10 kHz and decreases the frequency) to find the minimum frequency that generates pain relief with reduced paresthesia.

During, SCS parameter adjustment, the patient is asked to squeeze grip sensor 300 to provide a real-time indication of the amount of pain he or she is experiencing. If the amount of pain decreases, the patient loosens their grip, and releases grip sensor 300 completely if pain is absent. Conversely, if the pain increases, the patient grips more tightly. If a parameter set is applied that causes a spike in pain or generates a side effect (e.g., muscle activation), the patient responds with a conscious or reflexive squeezing of grip sensor 300 that will generate a rapid rise in measured grip force (via pressure sensor 310) and measured skin impedance (via GSR sensors 312). Additionally, changes in GSR may indicate stress or pain levels outside of the patient's own perception.

Parameter adjustment sessions may be conducted in an office/clinical setting or remotely. For remote sessions, the patient may be given grip sensor 300 for home use, and stimulation parameters are adjusted remotely by clinicians, or by the patient themselves.

Figure 5:
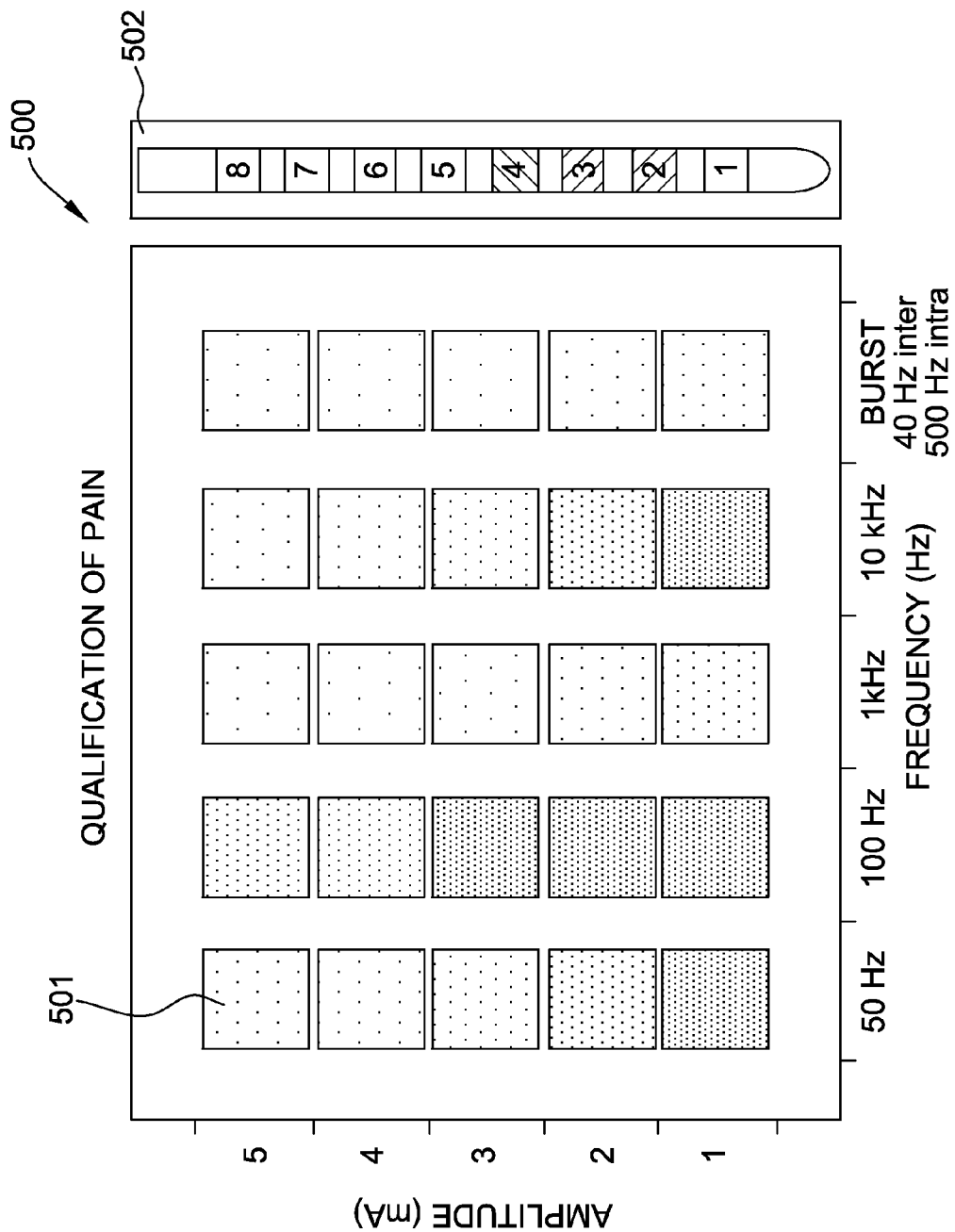
FIG. 5 is one embodiment of a pain quantification plot that may be produced using the grip sensor of FIG. 3.

FIG. 5 is one embodiment of a pain quantification plot 500 that may be displayed, for example, on a display device communicatively coupled to grip sensor 300 and/or computing device 400. Plot 500 shows pain results 501 for different parameters (i.e., amplitude and frequency) for tonic stimulation (the first and second columns), high-frequency stimulation (the third and fourth columns), and burst stimulation (the fifth column). In plot 500, for each pain result 501, denser patterns indicate higher amounts of pain, and less dense patterns indicate lower amounts of pain. In this embodiment, computing device 400 determines a pain level for each pain result 501 based on signals received from sensors (e.g., pressure sensors 310, GSR sensors 312) on grip sensor 300.

The pain level for each pain result 501 may be calculated using any suitable method. In this embodiment, all sensors on grip sensor 300 contribute to the calculation of the pain level.

For example, signals from pressure sensor 310 (shown in FIG. 3) may be analyzed within 1 second after a change in stimulation parameters, because there will likely be a sudden adjustment in grip strength of the patient in response to a change in pain levels. Quantification of pressure sensor signals may be performed in the time domain (e.g., calculating a pain level by rectifying and integrating) or in the frequency domain (e.g., calculating a pain level as a signal power of high-frequency components in the signal). Pressure sensor signals will generally decrease with lower pain levels, and increase with higher pain levels.

Signals from GSR sensors 312 may be analyzed, for example, over the first ten seconds after a change in stimulation parameters, because impedance will generally have a slow onset change in response to a change in pain levels. The measured impedance values will generally increase with lower pain levels (due to decreasing sweat) and decrease with higher pain levels (due to increasing sweat). Signals from other sensors, such as temperature sensors and heart rate sensors, may be analyzed similarly.

If pain levels change in response to a change in stimulation parameters, one would expect a time-synchronized, consistent change across all of the sensors. For example, if pain levels decrease for a given parameter set, one would expect a sudden decrease in pressure, and a gradual increase in measured impedance. The absolute change in pain level may be calculated as a weighted change in the pressure and GSR impedance signals. For example, each signal may be weighted as 50% of the total calculated change in pain level. Alternatively, any suitable weighting may be used. If both the pressure and GSR impedance signals do not change, or the signals change in an unexpected manner (e.g., pressure increase and GSR impedance increase), this may indicate that another factor caused the change in signals, and there is no quantifiable change in pain level.

Plot 500 also includes an electrode configuration display 502 that indicates the configuration of each electrode in an eight-electrode percutaneous SCS lead. In some embodiments, electrode configuration display displays a paddle lead instead. In this example, second and third electrodes are operating as cathodes, a fourth electrode is operating as an anode, and all other electrodes are inactive. As shown in plot 500, in this example, tonic stimulation at 100 Hz is generally not as effective as burst stimulation in decreasing pain. For a different set of anodic and cathodic electrode settings, the pain quantification plot may differ from that shown in plot 500.

For tonic stimulation, a range of parameters can be explored (e.g., using plot 500), and the parameters that generate maximum pain relief may be selected. Further, tonic stimulation parameters may be modified randomly to facilitate ensuring that the patient is unaware of the specific parameters used at any given time. Moreover, settings may be tested more than once to ensure a consistent response on pain levels is observed (e.g., switching back and forth between parameter set A and parameter set B). For burst stimulation and high-frequency stimulation, grip sensor 300 may be used in conjunction with the following algorithms.

FIGS. 6A-6C illustrate operation of one embodiment of a burst stimulation algorithm. To facilitate rational selection of burst stimulation waveform parameters, a burst stimulation algorithm starts by providing tonic stimulation at a fixed frequency (e.g., 50 Hz) (FIG. 6A). Parameters of the tonic stimulation are varied to determine a contact configuration, amplitude, and pulse width that generate paresthesia coverage of the target area. This contact configuration, amplitude, and pulse width are then kept constant for subsequent programming.

Next, as part of the burst stimulation algorithm, the stimulation is switched from one pulse to two pulse bursts (FIG. 6B), and a range of inter-burst frequencies (e.g., 10-100 Hz) and intra-burst frequencies (e.g., 500-1000 Hz) are explored to determine which inter-burst and intra-burst frequencies generate pain relief with reduced paresthesia. If no such relief is attainable, the stimulation is switched from two pulse bursts to three pulse bursts (FIG. 6C) and the frequency ranges are again explored for pain relief with reduced paresthesia. Switching to higher numbers of pulses is continued (e.g., 4 pulses, 5 pulses, etc.) until pain relief with reduced paresthesia is obtained.

Figure 7:
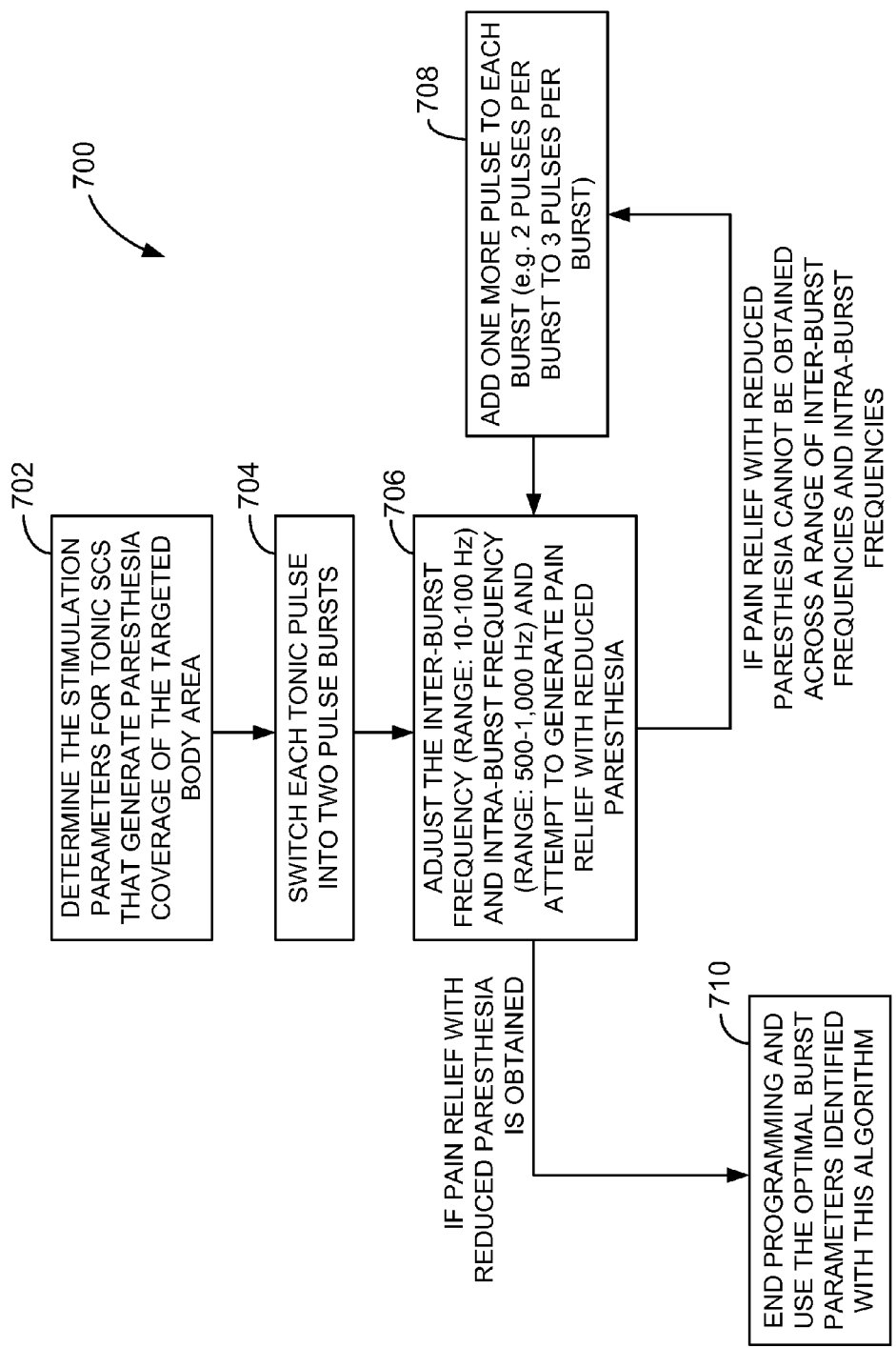
FIG. 7 is a flow chart of one embodiment of a burst stimulation algorithm.

For example, FIG. 7 is a flow chart of one embodiment of a burst stimulation algorithm 700. Algorithm 700 may be implemented, for example, using computing device 400 (shown in FIG. 4). At block 702, stimulation parameters for tonic SCS are determined that generate paresthesia overage of the targeted body area. At block 704, each single tonic pulse is switched into two pulse bursts. Subsequently, at block 706, a range of inter-burst frequencies (e.g., 10-100 Hz) and intra-burst frequencies (e.g., 500-1000 Hz) are adjusted in an attempt to generate pain relief with reduced paresthesia.

If pain relief with reduced paresthesia cannot be obtained by adjusting inter- and intra-burst frequencies, flow proceeds to block 708. At block 708, one more pulse is added to each pulse burst (e.g., two pulses per burst becomes three pulses per burst), and flow returns to block 706.

If pain relief with reduced paresthesia is obtained by adjusting inter- and intra-burst frequencies, flow proceeds to block 710. At block 710, stimulation programming is ended, and the optimal burst parameters identified with algorithm 700 are used for stimulation.

Similar to the burst stimulation algorithm, to facilitate rational selection of high-frequency stimulation waveform parameters, a high-frequency stimulation algorithm starts by providing tonic stimulation at a fixed frequency (e.g., 50 Hz). Parameters of the tonic stimulation are varied to determine a contact configuration, amplitude, and pulse width that generate paresthesia coverage of the target area. This contact configuration, amplitude, and pulse width are then kept constant for subsequent programming.

Next, as part of the high-frequency stimulation algorithm, the stimulation frequency is adjusted to lower threshold frequency (e.g., approximately 1 kHz), and slowly increased until pain relief with reduced paresthesia is obtained. Alternatively, the stimulation frequency may be adjusted to an upper threshold frequency (e.g., approximately 10 kHz), and slowly decreased until a minimum frequency at which pain relief with reduced paresthesia is still generated is reached.

Figure 8:
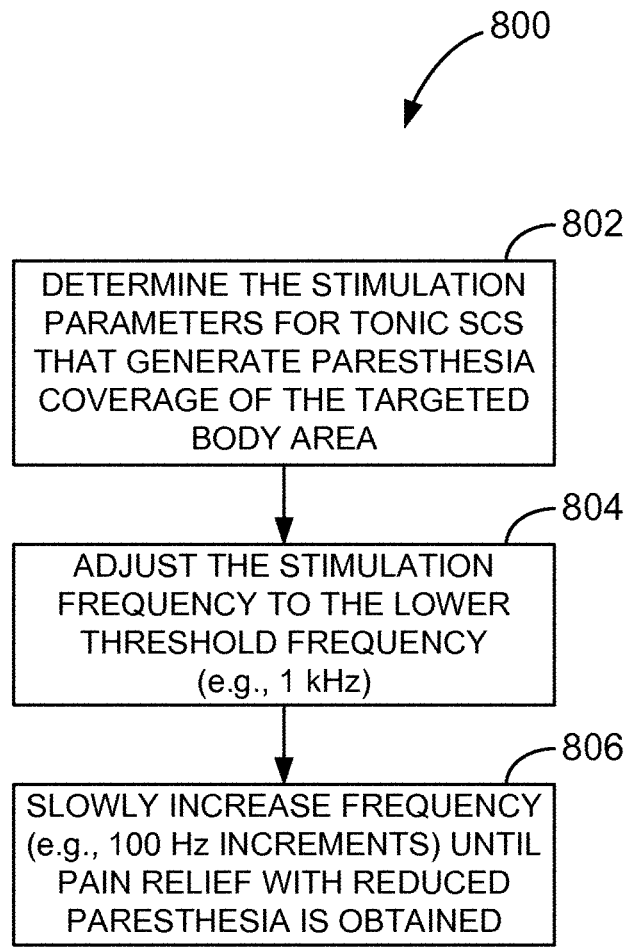
FIG. 8 is a flow chart of one embodiment of a high-frequency stimulation algorithm.

For example, FIG. 8 is a flow chart of one embodiment of a high-frequency stimulation algorithm 800. Algorithm 800 may be implemented, for example, using computing device 400 (shown in FIG. 4). At block 802, stimulation parameters for tonic SCS are determined that generate paresthesia overage of the targeted body area. At block 804, the stimulation frequency is adjusted to a lower threshold frequency (e.g., 1 kHz). Subsequently, at block 806, the frequency is increased relatively slowly (e.g., in increments of 100 Hz) until pain relief with reduced paresthesia is obtained.

Figure 9:
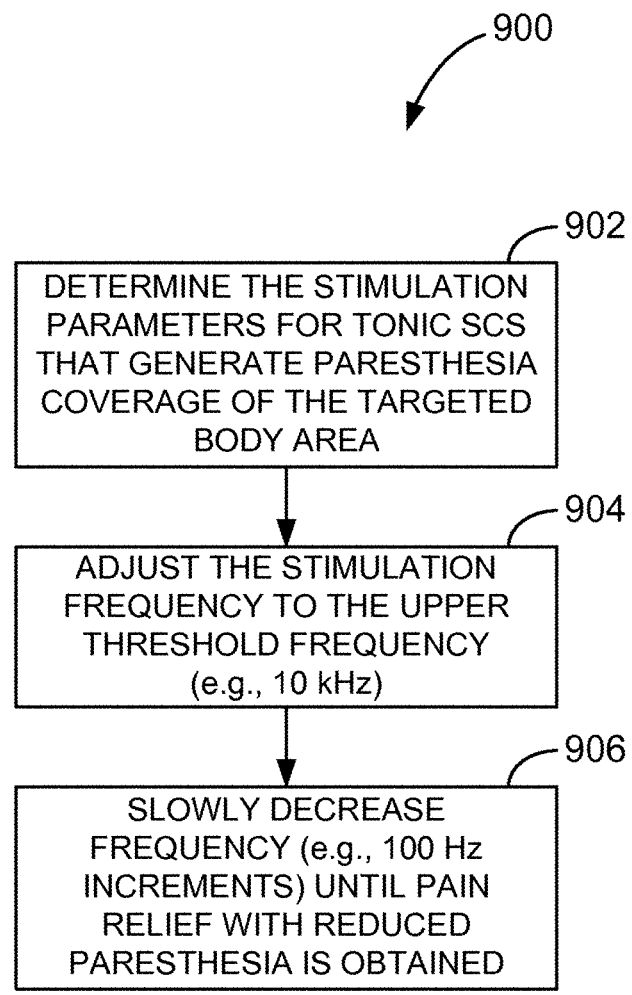
FIG. 9 is a flow chart of another embodiment of a high-frequency stimulation algorithm.

For example, FIG. 9 is a flow chart of another embodiment of a high-frequency stimulation algorithm 900. Algorithm 900 may be implemented, for example, using computing device 400 (shown in FIG. 4). At block 902, stimulation parameters for tonic SCS are determined that generate paresthesia overage of the targeted body area. At block 904, the stimulation frequency is adjusted to an upper threshold frequency (e.g., 10 kHz). Subsequently, at block 906, the frequency is decreased relatively slowly (e.g., in increments of 100 Hz) until pain relief with reduced paresthesia is obtained.

Figure 10:
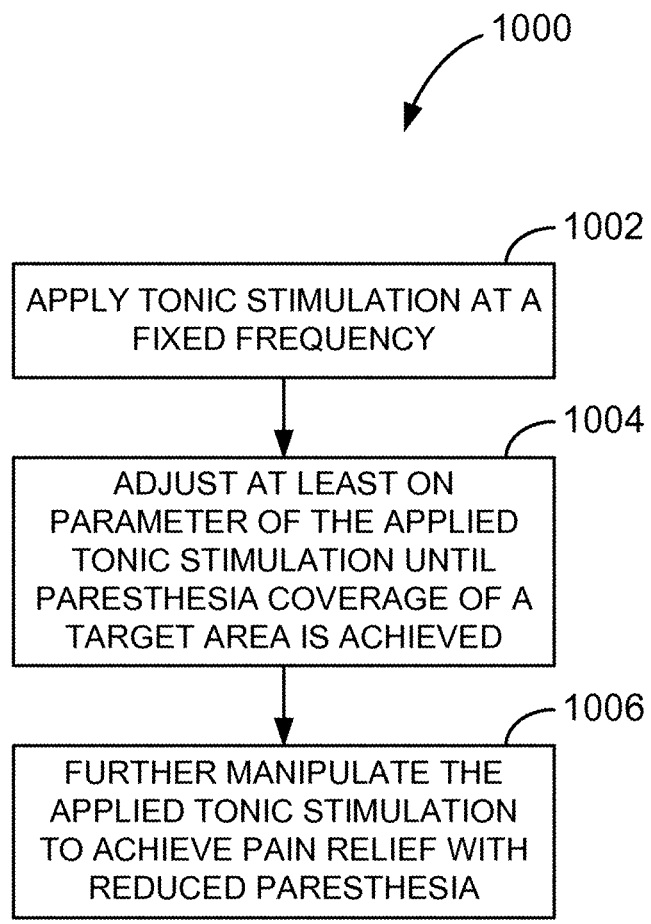
FIG. 10 is a flow chart of one embodiment of a method for determining SCS therapy parameters for a patient.

FIG. 10 is a flow chart of one embodiment of a method 1000 for determining SCS therapy parameters for a patient. Method 1000 may be implemented, for example, using computing device 400 (shown in FIG. 4). Method includes 1000 applying tonic stimulation at a fixed frequency at block 1002. At block 1004, at least one parameter of the applied tonic stimulation is varied until paresthesia coverage of a target area of the patient is achieved. Subsequently, at block 1006, the applied tonic stimulation is further manipulated to achieve one of burst stimulation and high-frequency stimulation that provides pain relief with reduced paresthesia. For example block 1006 may include one or more steps of algorithm 700 (shown in FIG. 7), algorithm 800 (shown in FIG. 8), and algorithm 900 (shown in FIG. 9).

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A grip sensor for quantifying pain experienced by a patient during spinal cord stimulation (SCS), the grip sensor comprising:
   an electronics enclosure;
   an annular outer shell substantially surrounding the electronics enclosure and sized to be held by the patient;
   a pressure sensor embedded in the outer shell and extending along the outer shell, the pressure sensor configured to measure a grip strength of the patient as SCS is applied to the patient; and
   a plurality of galvanic skin response (GSR) sensors configured to measure an electrical impedance of the skin of the patient as SCS is applied to the patient;
   wherein the electronics enclosure is configured to calculate a weighted change in SCS pain-related pressure and GSR impedance measurements from the pressure and galvanic skin response sensors, respectively, to obtain chances SCS-related pain levels in connection with changes in SCS parameters, the SCS-related levels to be provided to a display device for display.

2. The grip sensor of claim 1, further comprising a thermometer configured to measure a skin temperature of the patient as SCS is applied to the patient and to output an SCS pain-related temperature measurement to the electronics enclosure.

3. The grip sensor of claim 1, wherein the electronics enclosure and the outer shell form a substantially cylindrical housing.

4. The grip sensor of claim 3, further comprising:
   a first mechanical support member extending from a first end of the housing; and
   a second mechanical support member extending from a second end of the housing.

5. The grip sensor of claim 1, wherein the electronics enclosure is configured to:
   receive a SCS pain related temperature measurement from a thermometer; and
   calculate the pain levels based on the SCS pain-related pressure, impedance and temperature measurements.

6. The grip sensor of claim 1, wherein the display device displays the calculated SCS-related pain levels and the changes in the SCS parameters.

7. The grip sensor of claim 1, wherein the pressure sensor extends along a length of the outer shell and is placed within or underneath the outer shell.

8. The grip sensor of claim 1, wherein the electronics enclosure is configured to calculate a plurality of SCS-related pain levels based on the SCS pain related pressure measurements.

9. The grip sensor of claim 1, wherein the electronics enclosure is configured to calculate a plurality of SCS-related pain levels based the SCS pain related impedance measurements.

10. The grip sensor of claim 1, wherein the display device is configured to display a pain quantification plot that shows pain results associated with the different SCS parameters.

11. The grip sensor of claim 10, wherein the pain results comprise a first density pattern indicative of a first amount of pain and a second density pattern indicative of a second amount, of pain, the first and second density patterns determined by the electronics enclosure based on the SCS pain related pressure and impedance measurements.

* * * * *